United States Patent [19]
Bison et al.

[11] 3,932,441
[45] Jan. 13, 1976

[54] PROCESS FOR THE PRODUCTION OF PURE TETRAZOLE-1-ACETIC ACID

[75] Inventors: Günter Bison, Troisdorf; Walter Heinzelmann, Leverkusen; Norbert Linkat, St. Augustin; Wolfgang Wolfes, Mondorf, all of Germany

[73] Assignee: Dynamit Nobel Aktiengesellschaft, Germany

[22] Filed: Sept. 27, 1974

[21] Appl. No.: 509,858

[30] Foreign Application Priority Data
Sept. 28, 1973  Germany............................ 2348802

[52] U.S. Cl........................... 260/308 D; 260/308 D
[51] Int. Cl.²........................................ C07D 257/04
[58] Field of Search................................ 260/308 D

[56] References Cited
OTHER PUBLICATIONS
Can. J. Chem. 47 (1969), pp. 813–819.

*Primary Examiner*—Frederick E. Waddell
*Attorney, Agent, or Firm*—Craig & Antonelli

[57] ABSTRACT

Process for producing tetrazole-1-acetic acid of maximum purity includes the steps of providing a crude reaction product containing an alkyl ester of tetrazole-1-acetic acid having from 1 to 4 carbon atoms in the alkyl group, effecting molecular distillation of this reaction product at a temperature below 130°C. under a vacuum of $10^{-1}$ torr to obtain a distillant containing the alkyl ester and then gently hydrolyzing the resultant distillate to obtain the desired acid product.

5 Claims, 1 Drawing Figure

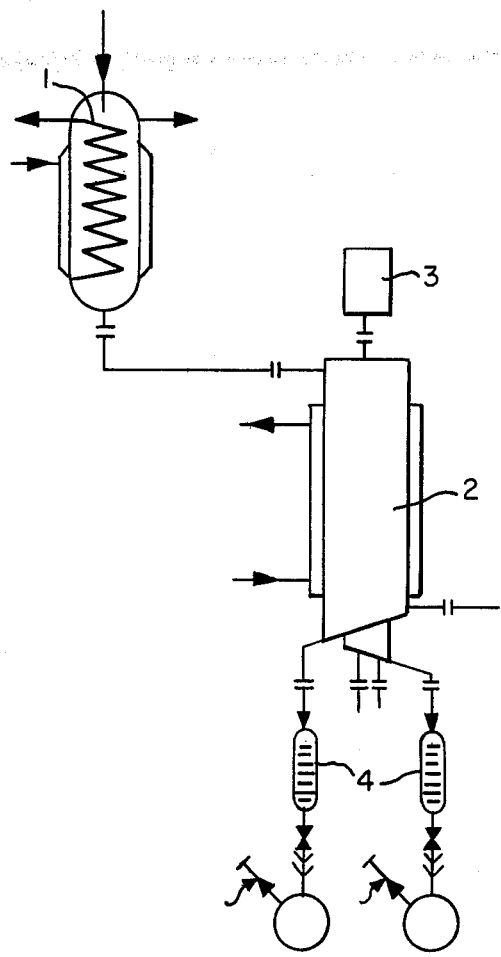

PROCESS FOR THE PRODUCTION OF PURE TETRAZOLE-1-ACETIC ACID

Various methods are conventional for the production of tetrazole-1-acetic acid (TAA-1) which in most cases proceed via the formation of TAA-1 alkyl esters, e.g. by:

1. The addition of $HN_3$ to the ethyl ester of isonitriloacetic acid as disclosed by Zimmermann & Olofson in "Tetrahedron Letters" No. 58 (1969), pp. 5081–84.
2. The addition of $HN_3$ to the ethyl ester of N-formimidic acid formed, for example, from glycine as disclosed by Hagedorn & Winkelmann in "Chemische Berichte" (Chemical Reports) 99 (1966), p. 853.
3. According to an analogous reaction as in (2), but designed as a one-stage process, wherein the ethyl ester of N-forminidic acid is formed from glycine ethyl ester hydrochloride or glycine- and trialkylorthoformate in a conventional manner, in the presence of $HN_3$, and is immediately cyclized to the tetrazole ring as disclosed by Fujisawa Pharmaceutical Co., Ltd., Osaka, in German Unexamined Laid-Open Application (DOS) 2,147,023 dated Sept. 21, 1971.
4. Tetrazole is reacted as the triethylamine salt with ethyl chloroacetate in acetone, thus producing a mixture of isomers of the ethyl ester of tetrazole-1-acetic acid and the corresponding ester substituted in the 2-position as disclosed by Raap & Howard in "Can. J. Chem." 47 (1969), pp. 813–19.

In all these reaction methods, a more or less strongly contaminated crude ester is obtained. Thus, for example, according to the process described in DOS 2,147,023, a black-brown crude ester is produced from which maximally 9% by weight of a crystalline component can be isolated after inoculation with crystals of the ester and, after a storage period of 48 hours at +4°C. Likewise, a deep-brown TAA-1 acid is formed with the use of glycine. Raap et al describe the possibility of separating the TAA-2 ester from the TAA-1 ester under vacuum by normal distillation with the remaining ester residue being saponified, and the tetrazole-1-acetic acid being subsequently subjected to a cumbersome purification process. Raap et al state expressly that the TAA-1 ethyl ester cannot be distilled.

It has now been found surprisingly that a completely pure TAA-1 acid is obtainable if one of its lower alkyl esters (e.g. methyl ester) is purified by distillation according to the procedure known as falling-film molecular distillation and is thereafter hydrolyzed without any further purification operation. Even maximum-purity TAA-1 acid is obtained by only a single molecular distillation step. This result is completely unexpected, because, on the one hand, Raap et al discloses that a lower alkyl ester of TAA-1 acid cannot be distilled without being decomposed, which is confirmed by the fact that, for example, the TAA-1 ethyl ester starts to decompose at 130°C. during a distillation test. On the other hand, however, it could nowise be foreseen, either, that according to the principle of molecular distillation, (causing no separating effect at all as known from normal distillation columns) an ester with a pure melting point is immediately obtained, which according to the analytical method of thin-layer chromatography, shows only traces of an impurity of far below one percent.

The procedure known as molecular distillation differs from a normal alembic distillation by the fact that the evaportion takes place from a product film, and the distillation path to the condenser is in the range of the mean free path of the gas molecules. The evaporation must be conducted at vacuums of below $10^{-1}$ torr (mm. Hg.). The process of molecular distillation is described in detail, for example, in "Ullmann's Encyklopaedie der technischen Chemie" (Ullmann's Encyclopedia of Technical Chemistry) (1969), Vol. 2/1, pp. 72–76 or in Houben Weyl, "Methoden der organischen Chemi" (Methods of Organic Chemistry) (1958), Vol. I/1, pp. 916–926.

Appropriate finished distillation units for this process are commercially available.

With the possibility of purifying a lower alkyl ester of TAA-1 acid, as a precursor of the acid, by means of molecular distillation, a path has been opened up for obtaining, according to a process technologically of maximum simplicity, tetrazole-1-acetic acid, which is of high interest for pharmaceutical products, with the required degree of purity (m.p. 128°–131°C.). Especially in case of TAA-1 acid, the purification according to known methods of recrystallization and treatment with bleaching agents, such as activated carbon or bleaching clay, has been hampered by very high losses and low efficiency.

With the aid of the molecular distillation, it is not only possible to separate more or less unknown impurities, as formed in the methods of $HN_3$-addition to isonitrile or the formimido ester, but it is furthermore feasible to separate the isomer mixture of TAA-1 ester and TAA-2 ester by distillation. In this process, though, it is necessary to operate with at least two stages under different vacuums.

The pressure to be maintained during the distillation must be below $10^{-1}$ torr; a lower limit cannot be set forth theoretically and is only defined by present technology. However, in practice, minimum pressures of around $10^{-3}$ torr can be attained by technically available plants. In general, the operation is carried out between $5 \times 10^{-2}$ and $10^{-3}$ torr.

The distillation temperature is dependent on the pressure. The run-off temperature of the distillation residue should not exhibit a temperature of above 130°C.; the optimum temperature of the evaporator surface for a technical distillation is between 95°C. and 120°C., and if the vacuum is very high (e.g. $10^{-4}$ torr.) temperatures below these values can also be utilized, such as, for example, between 70°C. and 95°C.

For conducting the falling-film molecular distillation, all conventional stills can be utilized, considering the aforementioned pressure and temperature ranges, the decisive considerations being the production of a thin film of the product to be distilled on a heated surface and an optionally cooled condensation surface, provided at a small spacing therefrom, e.g. 10 to 70 mm. Suitable are various systems with for example, a heated evaporator extending like a finger, which is fed from above and is provided with means for stripping off the product to be distilled, such as agitator coils, rollers, wiper blades, or the like, and with a tubular jacket as the condenser. Furthermore, feasible are systems with an externally heated jacketed evaporator fed from above, provided on the inside with corresponding, optionally rotatable scraping means which extend along the walls; the interior of this evaporator housing a condenser, for example in the form of a cooling finger. The interspace between the evaporator and the condenser can be evacuated by a high-vacuum pump, e.g. a mercury condensation pump.

In a vacuum zone arranged upstream thereof, with a somewhat lower vacuum of about $10^{-1}$ to $5 \times 10^{-2}$ torr, the removal of lower-boiling substances takes place at the same temperature, from the distilland running in a thin layer over, for example, a heating jacket or a coil.

Underneath the condenser, discharge devices are provided for the pure product, and underneath the evaporator, a drain to be heated is arranged for the unvaporized impurities.

The TAA-1 crude esters can be produced in various conventional ways. It is also possible, for example, first to prepare a crude TAA-1 acid and esterify the acid prior to the distillation process.

The thus-obtained TAA-1 alkyl esters are saponified according to known methods in water, optionally in a neutral or basic medium, preferably an acidic medium, e.g. ph of 1.0 to 4.0, the thus-formed acid itself catalyzing the hydrolytic saponification process. It is advantageous for the saponification operation to operate at temperatures of above 100°C. under normal pressure or at the excess pressure determined by the inherent (i.e. autogenous) pressure at the respective temperature; however, a temperature above 130°C. is not recommended.

It is also possible to conduct the process in a pressure vessel at up to 10 atmospheres and, for example, at 50°–120° C.

During the saponifying step, no further impurities are formed, so that, after crystallizing the TAA-1 acid from the supersaturated solution by cooling, the aqueous filtrate can be reused for a subsequent saponification. Accordingly, the yield in this operation is almost 100%.

Suitable lower alkyl esters of TAA-1 acid useful for the process of this invention are alkyl esters of 1–4 carbon atoms in the alkyl residue; although the limiting factor in this connection is primarily the physical characteristic of the boiling point, rather than chemical reasons. A $C_5$-ester of TAA-1 acid is distilled, at the attainable vacuums of around $10^{-3}$ torr, only at above 130°C. and thus undergoes decomposition, so that the essential criterion of the complete purity of the ester exclusively by distillation is no longer applicable.

Tetrazole-1-acetic acid serves as an intermediate, which itself is not pharmaceutically active, for the preparation of novel antibiotics such as, for example, 7-[2(1H-tetrazol-1-yl)-acetamido]-3-(2-methyl-1,3,4-thiadiazol-5-yl)-thiomethyl-3-cepheme-4-carboxylic acid.

The effected particular distillation usually is named molecular distillation because, in contrast to the conventionally used distillation, the space between the surface of the evaporator and the surface of the condensor is within or about the mean free path of a flying gaseous molecule.

Because this very narrow space another name is "short way evaporator" and owing the fact that raw material to be distilled flows down the evaporator and is distributed to a very thin skin on its heated surface another name is "fall-film distillator" resp. evaporator.

As now different types of such molecular distillation units are available the attached drawing should not limit the construction of usable distillation units and is only for informative purpose. The apparatus used in the examples is produced by Leybold-Heraeus at Hanau, Western Germany, and is designated as type KD 10-01. By the characteristics of instant molecular distillation process, as above all degasification prior the distillation, the short-way distillation itself and the way of collection of product running down after distillation, the process is independent of the process of production of raw tetrazole-1-acetic acid ester, though therefore the process of DOS 2,147,023 is preferred due to its relatively simple process measures.

The process of this invention will be further understood from the following examples:

EXAMPLE 1

Preparation of the Ester

According to the mode of operation described in DOS 2,147,023, Example 5, an experiment was conducted with ten times the amount of chemicals.

A mixture of 140 g. (1 mole) of glycine ethyl ester hydrochloride, 72 g. of sodium azide, 160 g. of methyl orthoformate and 200 ml. of glacial acetic acid are heated for 2 hours to 70°C. During this step, $HN_3$ concentrations are measured in the gas space of initially 16 vol. -%, dropping to approximately 4 vol. -%, with the aid of a calibrated, colorimetric method, wherein the azide-iron complex $[Fe(N_3)_6]$ of a dark-red color serves as the chromophore.

Thereafter, all volatile components are distilled off at 20 torr up to a bath temperature of 100°C. The residue is mixed with 2 liters of cold water and the thus-formed oil-water emulsion is combined with 2 liters of chloroform. After thorough mixing, the layers are separated, the aqueous layer is discarded, and the chloroform solution is dried with $Na_2SO_4$. After separating the chloroform by distillation, the residue is an oil (145 g.) having a deep dark-brown color.

After cooling to 0°C. and inoculation with pure ester, 14 g. of crystallized product can be obtained by vacuum filtering after 48 hours; these crystals still have a brownish discoloration due to adhering impurities and melt at 23°C. in their entirety. This 14 g. of crystallized product corresponds to 9% of theoretical yield. The production of sufficiently pure TAA-1 ethyl ester is, therefore, impossible to achieve by means of this crystallization procedure.

Purification of the Ester

The thus-produced oil, together with the 14 g. of crystallized product, is distilled by way of a laboratory molecular distillation unit as shown in the accompanying drawing.

During this procedure, the product first runs in a thin layer over a coil 1 heated to 90°C.; the applied vacuum is about $10^{-2}$ torr. This pretreatment is important to ensure a complete initial degasification of the product in order to maintain the vacuum required during the subsequent molecular distillation. For distilling purposes, the preliminary degasified product is applied dropwise to the heated evaporator 2, and is spread, with the aid of a coil or cylinder, as a thin film on the evaporator 2. The temperature of the distillation residue, measured underneath the evaporator, is 100°C. This coil is rotated by way of a magnetic clutch 3. Directly opposed to the evaporator is the jacket condenser. The vacuum obtained amounts to $5 \times 10^{-3}$ torr.

As a distillate 4, an almost colorless oil is collected which, after cooling to 0°C. overnight, is entirely crystallized (m.p. 32°–34°C.).

The distillation residue is a tarry product which solidifies very quickly, so that it is heated by means of infrared lamps to keep it flowable.

Yield:
112 g. of distillate = 72% of the theoretical amount based on the glycine ester employed.
33 g. of residue.

In accordance with analysis by thin-layer chromatography, only an impurity at the initial spot of <0.1% is found in addition to the TAA-1 ethyl ester. In the NMR spectrum, no signals can be found of isomers or impurities. The determined melting point of 32°–34°C. corresponds to the data for the pure ester disclosed in the literature.

Hydrolysis 156 g. (1 mole) of the TAA-1 ethyl ester distillate having a melting point of 32°–34°C. is refluxed for 1 hour with 300 ml. of approximately 10% strength hydrochloric acid. Alcohol is simultaneously distilled overhead. By cooling to room temperature under agitation, the TAA-1 acid is crystallized. After thorough filtering over a suction filter and drying of the filter cake at 100°C. in a circulation drying chamber, 102 g. of TAA-1 acid (79.5% of theory) is obtained with a melting point of 128°–131°C. To obtain a TAA-1 acid which is completely free of HCl, the acid can once more be crystallized from $H_2O$.

The aqueous-hydrochloric filtrate can be resued for a subsequent batch.

The total yield, including the amount obtained from the filtrate is 122 g. of TAA-1 acid = 95.5% of theory.

EXAMPLE 2

In a manner corresponding to Example 1, molecular distillation is utilized to purify (a) the methyl ester and (b) the n-butyl ester of TAA-1 acid and then the acid is obtained by hydrolysis. Likewise high yields and equally high purity could thus be attained, i.e.:

| ESTER | YIELD | PURITY OF ACID |
| --- | --- | --- |
| Methyl ester | 63% | 99.7 – 99.9%(by titration) |
| N-butyl ester | 58% | 99.6 – 99.9%(by titration) |

While the novel principles of the invention have been described, it will be understood that various omissions, modifications and changes in these principles may be made by one skilled in the art without departing from the spirit and scope of the invention.

What is claimed is:

1. In a process for the production of tetrazole-1-acetic acid from a crude reaction product containing an ester of said acid, wherein the crude reaction product is treated to isolate the ester and the ester is hydrolyzed to form the acid, the improvement which comprises effecting a falling-film molecular distillation of the reaction product that contains an alkyl ester of tetrazole-1-acetic acid with 1–4 carbon atoms in the alkyl group at temperatures of below 130°C. under a vacuum of $<10^{-1}$ torr to obtain a distillate containing a purified alkyl ester which can be hydrolyzed to provide tetrazole-1-acetic acid of maximum purity.

2. The process of claim 1, wherein distillation is effected at a temperature above 70°C. and a vacuum to $10^{-4}$ torr.

3. The process of claim 1, wherein the distillation is effected at a temperature between 95°C. and 120°C. and at a vacuum between $5x^{-2}$ and $10^{-3}$ torr.

4. The process according to claim 1, wherein the vacuum is $10^{-4}$ torr and the temperature is between 70° and 95°C.

5. The process of claim 1, wherein the molecular distillation is effected by producing a thin film of the reaction product on a heated surface spaced from a condenser surface from 10 to 70 mm.

* * * * *